United States Patent
Nakada

[11] Patent Number: 5,190,079
[45] Date of Patent: Mar. 2, 1993

[54] FLOW CONTROL DEVICE

[75] Inventor: Tsuneo Nakada, Yamanashi, Japan

[73] Assignee: Terumo Kabushiki Kaisha, Tokyo, Japan

[21] Appl. No.: 750,728

[22] Filed: Aug. 20, 1991

Related U.S. Application Data

[63] Continuation of Ser. No. 657,337, Feb. 15, 1991, abandoned, which is a continuation of Ser. No. 339,190, Apr. 14, 1989, abandoned.

[30] Foreign Application Priority Data

Apr. 15, 1988 [JP] Japan .................................. 63-92854
May 23, 1988 [JP] Japan .................................. 63-126846

[51] Int. Cl.$^5$ .............................................. F15D 1/02
[52] U.S. Cl. ..................................... 138/45; 138/46; 251/6; 604/250
[58] Field of Search ...................... 138/40, 44, 45, 46; 251/4, 6, 7; 604/250

[56] References Cited

U.S. PATENT DOCUMENTS

| | | | |
|---|---|---|---|
| 3,630,481 | 12/1971 | McGay | 251/6 |
| 3,893,468 | 7/1975 | McPhee | 251/6 |
| 4,013,263 | 3/1977 | Adelbery | 251/6 |
| 4,087,301 | 5/1978 | Steadman | 138/45 |
| 4,238,108 | 12/1980 | Muetterties | 251/6 |
| 4,340,201 | 7/1982 | Becker | 251/6 |
| 4,475,708 | 10/1984 | Becker | 251/6 |
| 4,475,709 | 10/1984 | Becker | 251/6 |
| 4,725,037 | 2/1988 | Adelbery | 251/6 |
| 4,856,755 | 8/1989 | Clarke | 251/6 |
| 4,869,721 | 9/1989 | Karpisek | 251/6 |
| 4,895,340 | 1/1990 | Forbery | 251/6 |
| 4,919,389 | 4/1990 | Hoekwater et al. | 251/6 |
| 4,974,811 | 12/1990 | Ishida | 604/250 |

FOREIGN PATENT DOCUMENTS

| | | |
|---|---|---|
| 19497/70 | 3/1972 | Australia . |
| 19436/76 | 5/1978 | Australia . |
| 42555/78 | 10/1979 | Australia . |
| 66454/81 | 6/1981 | Australia . |

Primary Examiner—James E. Bryant, III
Attorney, Agent, or Firm—Frishauf, Holtz, Goodman & Woodward

[57] ABSTRACT

A flow control device for controlling the rate of flow liquid wherein a liquid supply tube is inserted in a liquid supply tube insertion channel extending in the longitudinal direction of the liquid supply tube. A roller is provided for squeezing the liquid supply tube against the bottom of the tube insertion channel. Ridges are provided for squeezing the opposite side edges of the liquid supply tube to a greater degree than the central portion of the liquid supply tube. The bottom of the insertion channel has a first inclined surface inclined with respect to roller bearing grooves for fine adjustment of the rate of liquid flow, and a second inclined surface terminating in the first inclined surface and inclined in the same direction as the first inclined surface but by a greater angle than the first inclined surface for a coarser adjustment of liquid flow through the liquid supply tube.

8 Claims, 4 Drawing Sheets

FLOW CONTROL DEVICE

This application is a continuation of application Ser. No. 07/657,337, filed Feb. 15, 1991, (now abandoned) which is a continuation of Ser. No. 07/339,190 filed Apr. 14, 1989 (now abandoned).

BACKGROUND OF THE INVENTION

This invention relates to a flow control device used for controlling the rate of flow of liquid passing through a liquid supply tube of a liquid transfer set, such as a solution administration set.

FIGS. 1 to 3 show a prior art liquid flow device of this type. As is shown, the device comprises a housing 1 with a liquid supply tube insertion channel 2. Opposite side walls of the liquid supply tube insertion channel 2 are formed with bearing grooves 4 (FIGS. 2 and 3). A manually movable roller 3 has its shaft 3b mounted in the bearing grooves 4 such that it is movable along the liquid supply tube insertion channel 2. The liquid supply tube insertion channel 2 has a bottom surface 2a which is inclined by a predetermined (FIG. 3) angle with respect to the bearing grooves 4. A liquid supply tube 5 is passed through the bottom surface 2a and periphery 3a of the roller 3. The roller 3 is manually moved to be closer to or remoter from the bottom surface 2a of the liquid supply tube insertion channel 2 to vary the extent of squeezing of the liquid supply tube 5 so as to control the rate of flow of liquid.

In the above prior art flow control device, the liquid supply tube 5 is made of a soft thermoplastic polymer such as polyvinyl chloride and is therefore subject to a phenomenon of creep. Squeezed opposite edges of the liquid supply tube initially have strong restoring force and tend to restore to the initial state. In long use, however, the restoring force becomes weaker, so that the initially formed inner flow passage of the liquid supply tube 5 is changed in long use. This means that it is difficult to obtain a stable rate of flow.

In a different aspect, with the prior art flow control device it is necessary to provide a wide range of rate of flow, from zero to a very high rate. Also, a certain limitation is imposed on the length of the housing 1 by considerations of the durability and operability. Therefore, it is difficult to reduce the inclination of the bottom surface 2a of the liquid supply tube insertion channel 2. This means that it is difficult to obtain flow control, particularly fine flow control.

Other prior art pertaining to the flow control device according to the present invention includes Japanese Patent Disclosures 47-1540, 50-41374, 52-81718, 52-108691, 52-142331, 53-103685, 53-144191, 53-148193, 54-2515, 54-10426, 54-10427, 54-60792, 54-108492, 55-72986, 58-30593, 61-41462, 50-125591, 50-125592 and 51-102392, Japanese Utility Model Disclosures 53-18089, 53-42499, 54-3096, 54-66697, 54-72398, 54-183196, 55-2338, 57-12868, 57-188976, 57-194958, 57-194959, 58-58150, 58-58151, 59-5939, 59-88563, 5992265, 61-151742, 61-156935, 61-180042, 61-180043 and 54-131395, Japanese Patent Publications 48-36526, 55-27986, 55-27987, 55-31351, 57-8342, 60-27870, 55-8573, 56-43578, 56-49013, 58-22224 and 58-44384, Japanese Utility Model Publications 51-45911 and 59-9642 and Japanese Patent Announcement 56-501619.

SUMMARY OF THE INVENTION

This invention has been developed in view of the above problems, and its object is to provide a flow control device, which can reduce flow rate changes in long use and ensures a stable flow at all times.

Another object of the invention is to provide a flow control device, which provides a wide range of flow rates from zero to a very high rate with an ordinary housing length and permits accurate flow control, particularly in a fine flow control range.

To attain the above objects of the invention, there is provided a flow control device with a flexible liquid supply tube mounted therein such that said liquid supply tube can be squeezed by making use of its flexibility to vary the size of a flow path in said tube to thereby effectively control the rate of flow of liquid through said tube, said flow control device comprising a housing having a liquid supply tube insertion channel, through which said liquid supply tube is inserted, said insertion channel having a bottom, a roller mounted in said housing for movement along said liquid supply tube insertion channel from one end to the other end thereof such that said roller gradually approaches the bottom of said liquid supply tube insertion channel to squeeze said liquid supply tube in said insertion channel as said roller moves toward said other end, and urging or squeezing means for urging opposite edges of said liquid supply tube inserted in said insertion channel extending in the longitudinal direction of said liquid supply tube.

The urging means may be a pair of substantially continuous ridges extending along the opposite edges of the bottom of said liquid supply tube insertion channel in the direction of movement of said roller and in a range of movement of said roller.

The urging means also may be a pair of substantially continuous ridges formed on the opposite edges of the periphery of said roller so as to be in contact with said liquid supply tube.

The urging means further may be a plurality of substantially continuous ridges formed on opposite edges of the bottom of said liquid supply tube insertion channel extending in the direction of movement of said roller and also on opposite edges of the periphery of said roller so as to be in contact with said liquid supply tube.

With the flow control device having the above construction according to the invention, after mounting the liquid supply tube by inserting it in the liquid supply tube insertion channel, the rate of flow in the tube is controlled by moving the roller from one end toward the other end. With the movement of the roller, the liquid supply tube is squeezed at its opposite ends in sectional view (where the phenomenon of creep is pronounced) with the ridges. As a result, opposite edges of the squeezed liquid supply tube are reliably secured. In the liquid supply tube, a flow path is formed not at opposite end portions in sectional view but in a central portion which is substantially free from creep. Thus, changes in the flow rate in long use can be reduced, and a stable flow can be obtained at all times. The ridges may be formed to have round sectional profiles to avoid damage to the liquid supply tube.

According to the invention, there is further provided a flow control device with a flexible liquid supply tube mounted therein such that said liquid supply tube can be squeezed by making use of its flexibility to vary the size of a flow path in said tube to thereby effectively control the rate of flow of liquid through said tube, said flow control device comprising a housing having a liquid supply tube insertion channel, through which said liquid supply tube is inserted, and the opposite side walls of which are formed with bearing grooves extending in the longitudinal direction of said liquid supply tube insertion channel, said insertion channel having a bottom, and a roller having a shaft supported in said bearing grooves such that said roller can be moved along said liquid supply tube insertion channel from one end to the other end, said liquid supply tube in said liquid supply tube insertion channel being squeezed by the periphery of said roller, said bottom of the liquid supply tube insertion channel including first and second inclined surfaces which are inclined with respect to said bearing grooves and which are co-operative with said roller to squeeze said liquid supply tube for control of the rate of flow of liquid through said liquid supply tube, said first inclined surface being adapted for fine adjustment of rate of flow, and said second inclined surface being inclined in the same direction as said first inclined surface but by a greater angle than said first inclined surface.

The one end of the second inclined surface may terminate in one end of the first inclined surface.

Further, one end of a third inclined surface which is inclined with respect to the bearing grooves may terminate in the other end of the first inclined surface.

With the flow control device having the above construction according to the invention, the rate of flow of liquid is brought to be zero, that is, the liquid supply is stopped, by moving the roller to one end of the liquid supply tube insertion channel. When it is desired to start from this state liquid supply at a very slight rate, the roller is moved from its zero flow rate position to a position corresponding to the first inclined surface. At this position, liquid can be supplied at a very slight rate. When it is desired to supply liquid at a very high rate, the roller is moved to a position corresponding to the second inclined surface, which has a greater inclination angle than the first inclined surface of the bottom of the liquid supply tube insertion channel. At this position, liquid can be supplied at a very high rate.

Further, with the ridges provided on opposite edges of the bottom of the liquid supply tube insertion channel extending in the direction of movement of the roller and also on opposite edges of the periphery of the roller so as to be in contact with the liquid supply tube, the liquid supply tube is squeezed at opposite end portions in sectional view where the phenomenon of creep is pronounced, so that the opposite edges of the liquid supply tube are reliably secured. Thus, the flow path of the liquid supply tube is formed not at opposite end portions in sectional view but in a central portion which is substantially free from creep. The flow rate changes in long use thus can be reduced to provide further improvement of the accuracy of the flow control.

DETAILED DESCRIPTION

Now, some preferred embodiments of the invention will be described with reference to the drawings.

Figure 1:
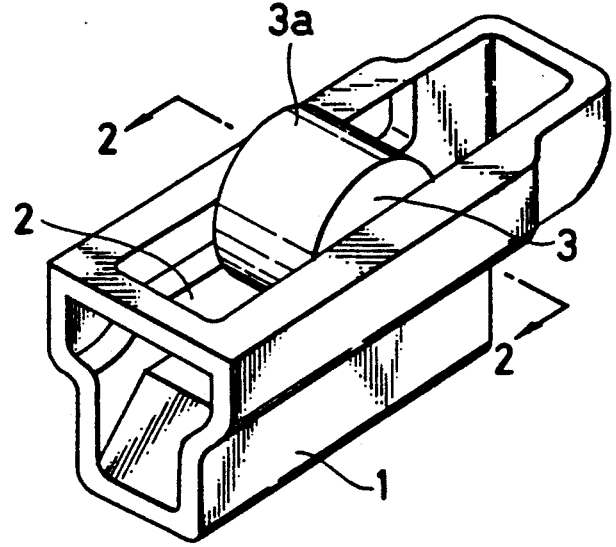
FIG. 1 is a perspective view showing a prior art flow control device.
Figure 2:
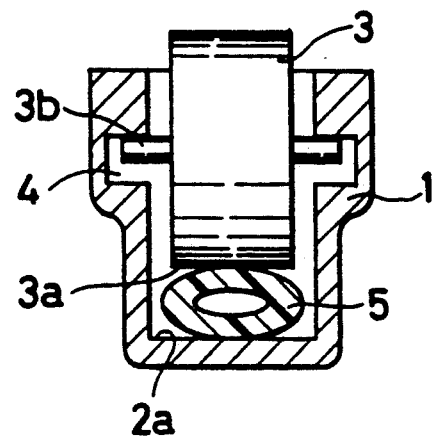
FIG. 2 is a sectional view taken along line 2—2 in FIG. 1.
Figure 3:
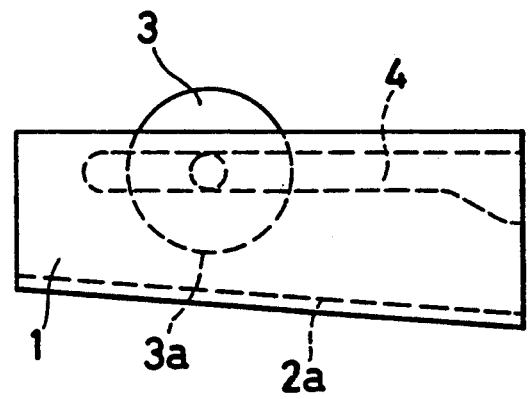
FIG. 3 is a side view of the prior art device shown in FIG. 1.
Figure 4:
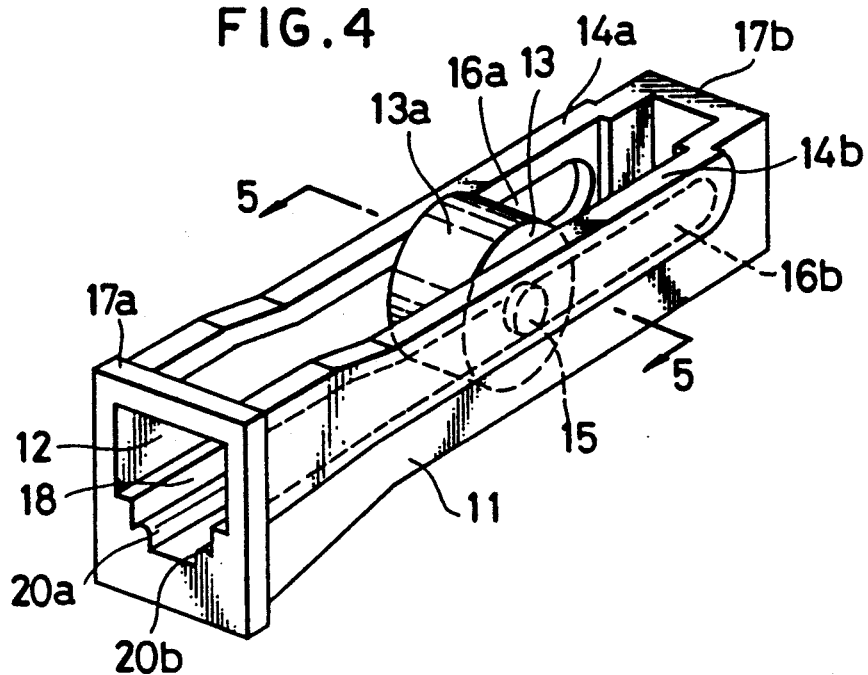
FIG. 4 is a perspective view showing one embodiment of the flow control device according to the invention.

FIG. 4 is a perspective view showing one embodiment of the flow control device according to the invention. In the Figure, reference numeral 11 designates a substantially rectangular housing made of a hard polymer material. In the housing 11, groove-like space 12 is formed extending in its longitudinal direction. A manually movable roller 13 is mounted in the space 12 for movement in the longitudinal direction of the insertion channel. More specifically, opposed wall surfaces 14a and 14b of the housing 11 are formed with bearing grooves 16a and 16b to support and guide a shaft 15 of the roller 13 in the longitudinal direction of the housing 11. The roller 13 partly projects from the housing 11, and it can be rotated by operating its projecting portion with a finger. The longitudinally opposite ends of the housing 11 are provided at the top with reinforcement frames 17a and 17b each intervening between the side walls 14a and 14b. When the roller 13 is moved to one end of the space 12, the shaft 15 strikes ends of the bearing grooves 16a and 16b so that the roller can no further be moved.

It will be seen that the roller 13 can be moved in the space 12 along the bearing grooves 16a and 16b in the longitudinal direction of the housing 11. The liquid supply tube insertion channel 18 is defined such that it constitutes the bottom of the space 12, and it extends in the longitudinal direction thereof and faces the periphery 13a of the roller 13. The bottom surface of the liquid supply tube insertion channel 18 constitutes an inclined surface inclined at a fixed angle to the bearing grooves 16a and 16b from one end to the other end of the bearing grooves. Thus, as the roller 13 is manually moved from one end toward the other end of the bearing grooves 16a and 16b, its periphery becomes closer and closer to the bottom of the liquid supply tube insertion channel 18 to squeeze the liquid supply tube inserted in the insertion channel 18, thus effecting the flow rate control.

Figure 5:
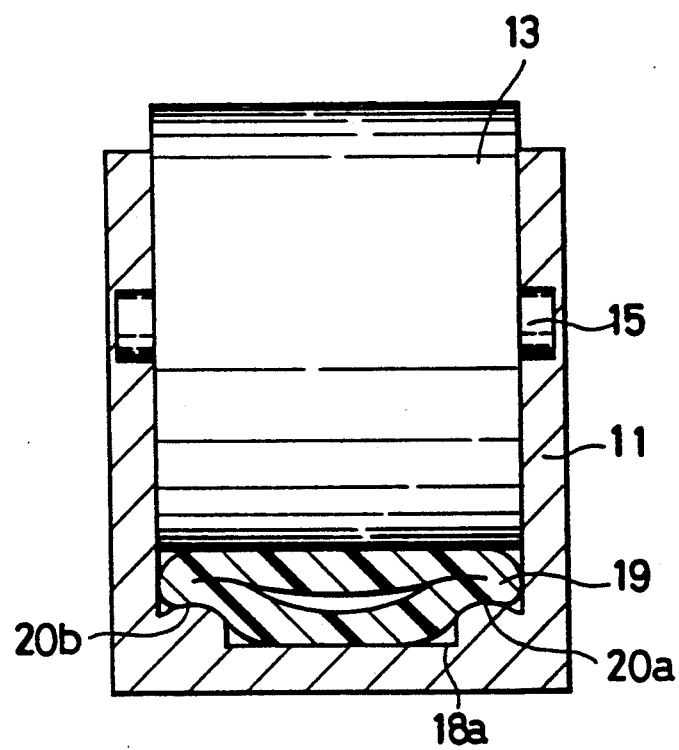
FIG. 5 is a sectional view taken along line 5—5, to an enlarged scale, showing the device shown in FIG. 4 with a liquid supply tube mounted therein.

FIG. 5 is a sectional view taken along line 5—5 in FIG. 4, showing the device with a liquid supply tube 19 made of a soft polymer material mounted in the liquid supply tube insertion channel 18. Opposite edges of the bottom 18a of the liquid supply tube insertion channel 18 are provided with ridges 20a and 20b serving as liquid supply tube urging means, which extend in the longitudinal direction and have a concave top surface. The liquid supply tube 19 is squeezed more strongly at its opposite end portions in sectional view than at its central portion between the ridges 20a and 20b on one hand and the periphery 13a of the roller 13 on the other hand. In this way, the liquid supply tube 19 is reliably secured, and changes in the rate of flow in the liquid supply tube 19 in long use are prevented.

In specific numerical figures, when using a roller with an outer diameter of 14 mm and a width of 4.7 mm as the roller 13 and a liquid supply tube made of polyvinyl chloride and with an outer diameter of 3.3 mm and a wall thickness of 0.6 mm as the liquid supply tube 19, it is desired to set the width x of the roller 13 and width y of the liquid supply tube insertion channel 18 of the housing 11 to be in a relation:

$$0.2 \text{ mm} < -y < 0.4 \text{ mm}$$

In other words, strong contact between each side surface of the roller 13 and a corresponding side wall of the liquid supply tube insertion channel 18 precludes looseness of the roller 13 due to the elasticity of the liquid supply tube 19 and prevents changes in the size and shape of the liquid supply tube insertion channel 18 in long use.

It is also possible to prevent changes in the size and shape of the liquid supply tube insertion channel 18 by setting the axial length x' of the roller 13 and mounting width y' of the roller shaft 15 in the housing 11 to be in a relation:

$$0.2 \text{ mm} < x' - y' < 0.4 \text{ mm}$$

The ridges 20a and 20b suitably have their height set to 0.2 to 0.8 mm, width to 0.5 to 1.0 mm and radius R of curvature to 0.3 to 1.0 mm.

With the flow control device having the above construction, after positioning the roller 13 at one end of the liquid supply tube insertion channel 18 the liquid supply tube 19 is inserted in the insertion channel 18 and set at a desired position. Then, the roller 13 is rotated with a finger. The roller 13 thus rolls over the liquid supply tube 19 toward the other end of the insertion channel 18. This movement of the roller 13 squeezes the liquid supply tube 19 and effects control of the rate of flow of liquid in the tube.

Since the opposite edges of the bottom of the liquid supply tube insertion channel 18 are provided with the ridges 20a and 20b, the liquid supply tube 19 is squeezed at its opposite end portions in sectional view where the phenomenon of creep is pronounced. Thus, the opposite end portions of the liquid supply tube noted above are reliably secured, and the phenomenon of creep is prevented.

Further, since the roller 13 is firmly engaged in the liquid supply tube insertion channel 18, the insertion channel 18 will never be changed in size or shape in long use. Thus, the liquid supply tube 19 is never deformed, and a stable rate of flow can be obtained.

Figure 6:
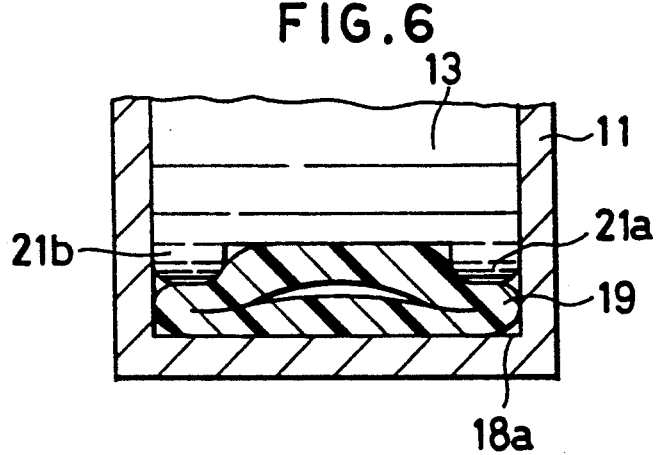
FIG. 6 is a fragmentary sectional view showing a different embodiment of the flow control device according to the invention.

In the above embodiment, the ridges 20a and 20b for prevention of creep are provided on the side of the liquid supply tube insertion channel 18. However, it is possible to provide the ridges on the side of the roller 13 as well, as shown in FIG. 6. More specifically in this case ridges 21a and 21b are formed on opposite edge portions of the periphery 13a of the roller 13.

With this construction, the liquid supply tube 19 is squeezed between the ridges 21a and 21b on the roller 13 and opposite edges of the bottom surface 18a of the liquid supply tube insertion channel 18. In this way, creep of the liquid supply tube 19 can be prevented.

It is of course possible to provide ridges on opposite edges of the periphery 13a of the roller 13 and bottom surface 18a of the liquid supply tube insertion channel 18. These ridges may be formed separately from the housing and roller 13. These ridges, as urging means, may not be continuous and may have any desired shape so long as they can substantially prevent creep of opposite edges of the squeezed liquid supply tube 19.

The present inventor conducted the following experiment to confirm the effect of the invention.

A flow control device as shown in FIG. 4 was used, which comprised a manually movable roller made of ABS (acrylonitrile-buthadiene-styrene copolymer) and a housing made of polyethylene. A liquid supply tube made of polyvinyl chloride was mounted in the device for measuring the rate of change in number of drops. Opposite edges of the bottom surface of the liquid supply tube insertion channel of the housing were provided with ridges with a height of 0.5 mm, a width of 0.7 mm and a radius R of curvature of 0.6 mm.

Further, the width of the surface in contact with the roller was set to 4.7 mm, and the width of the liquid supply tube insertion channel on the housing side was set to 4.4 mm.

For the measurement of the rate of change in number of drops, a solution administration set as the liquid transfer set using the above flow control device and liquid supply tube was coupled to a dripping bottle containing a medicine. The liquid transfer rate was adjusted to 60±5 drops per minute, and then the number of drops per minute was measured for 60 minutes. The maximum rate of change in number of drops was obtained as Maximum rate of change in number of drops (%) =

$$\frac{\left(\begin{array}{c}\text{Maximum or minimum} \\ \text{drop number in 60 min.}\end{array}\right) - \left(\begin{array}{c}\text{Initially set} \\ \text{drop number}\end{array}\right)}{\text{Initially set drop number}} \times 100$$

One drop was set to about 1/15 cc and to about 1/60 cc. Table 1 shows the results of measurement in case of about 1/15-cc drops, and Table 2 shows the results in case of about 1/60-cc drops:

TABLE 1

|  | Average (%) | Maximum (%) | Minimum (%) |
|---|---|---|---|
| Prior Art (n = 5) | −37.6 | −33.1 | −45.0 |
| Invention (n = 30) | −5.3 | +4.3 | −11.7 |

TABLE 2

|  | Average (%) | Maximum (%) | Minimum (%) |
|---|---|---|---|
| Prior Art (n = 5) | −64.7 | −58.5 | −72.2 |
| Invention (n = 30) | −6.6 | +22.2 | −37.0 |

It will be seen from the above results that with the product according to the invention changes in number of drops are small compared to the prior art product, that is, it is possible to obtain steady drop number accuracy at all times.

It is to be appreciated that with the above embodiment of the flow control device, in which substantially continuous ridges are provided on opposite edges of the bottom surface of the liquid supply tube insertion channel in the housing and opposite edges of the periphery of the roller, it is possible to prevent flow rate changes that might otherwise occur due to creep of the liquid supply tube, a stable rate of flow can be obtained at all times.

Figure 7:
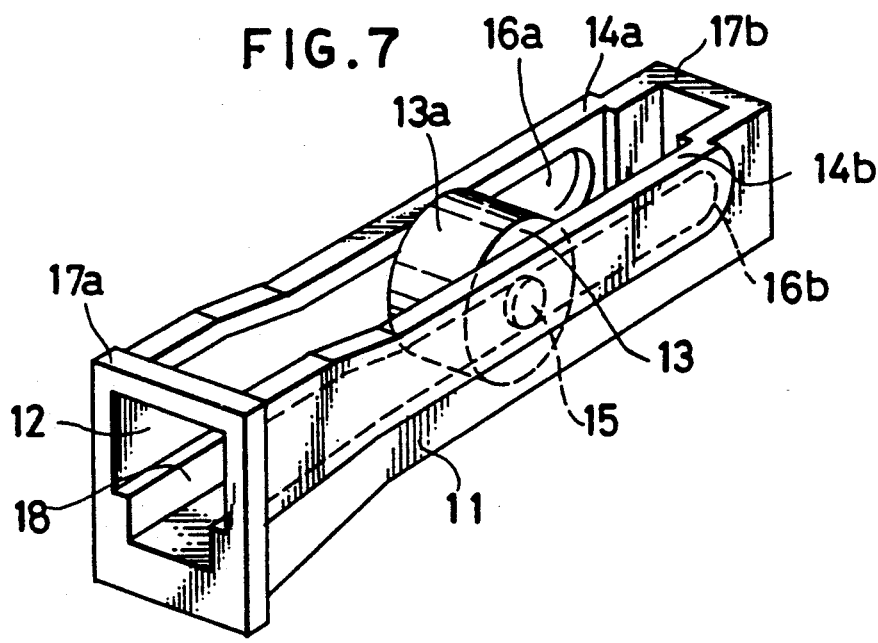
FIG. 7 is a perspective view showing a further different embodiment of the flow control device according to the invention.
Figure 8:
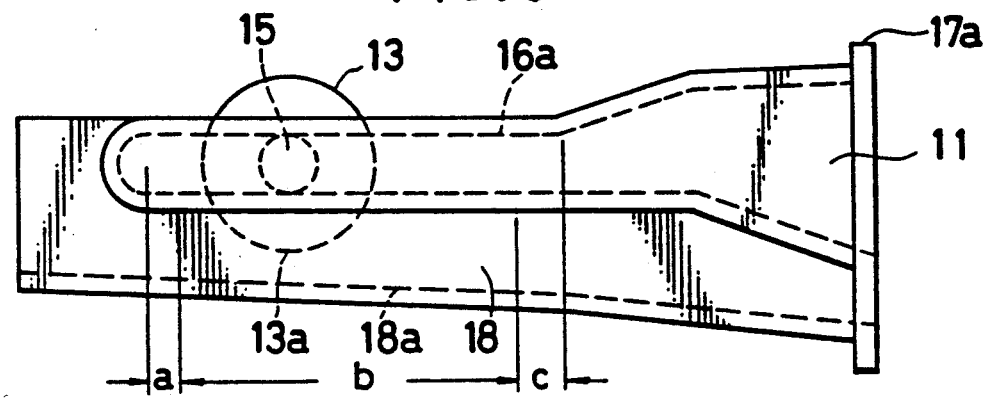
FIG. 8 is a side view showing the device shown in FIG. 7.

FIGS. 7 and 8 show a different embodiment of the flow control device according to the invention. Parts like those in FIGS. 4 and 5 are designated by like reference numerals with omission of the description.

Figure 9:
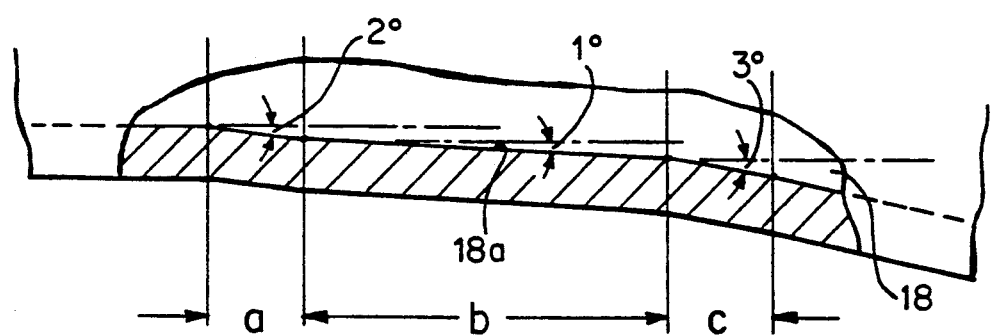
FIG. 9 is an enlarged fragmentary view showing the bottom surface 18a of FIG. 8 in greater detail, wherein the angles are exaggerated for clarity.

In this embodiment, the inclined surface of the bottom 18a of the liquid supply tube insertion channel 18, over the portion therefor which co-operates with the roller 13 in squeezing the liquid supply tube 19 to control the rate of flow of liquid in the tube 19 comprises a plurality of, in this embodiment three, different inclined surfaces (b) as a first inclined surface, (c) as a second inclined surface, and (a) as a third inclined surface, continuous to one another and corresponding to respective rates of supply of liquid, as shown in FIGS. 8 and 9. These inclined surfaces (a) to (c) have respective lengths and inclination angles as shown in Table 3.

Although the inclined surfaces (a) to (c) are shown to be linear in FIG. 8, actually they are curved at the borderline between adjacent ones of them as shown in FIG. 9, wherein the angles are shown in exaggerated form.

TABLE 3

| Portion | Length | Inclination angle |
|---|---|---|
| a | 2 mm | 2° |
| b | 20 mm | 1° |
| c | 4 mm | 3° |

Preferably, opposite side edges of the inclined surfaces (a) to (c) of the bottom 18a of the liquid supply tube insertion channel 18 are provided with ridges 20a and 20b (like in FIG. 5) extending in the longitudinal direction and having a curved top surface. The opposite edges of the liquid supply tube 19 are squeezed more strongly than the central portion between the ridges 20a and 20b on one hand and the periphery 13a of the roller 13 on the other hand.

Thus, it is possible to reliably secure the liquid supply tube 19, prevent large flow changes in the liquid supply tube 19 over a long time and improve the accuracy of the flow rate control.

With the flow control device having the above construction, the roller 13 is moved to one end (left end in FIG. 8) of the liquid supply tube insertion channel 18 to stop the liquid supply. At this position, the inclined surface (a) of the bottom 18a of the liquid supply tube insertion channel 18 facing the periphery 13a of the roller 13 is inclined at a fixed angle of 2°.

Therefore, the liquid supply can be reliably stopped even if there are fluctuations of the thickness of the wall of the liquid supply tube 19. To supply liquid at a very slight rate, the roller 13 is moved to a position corresponding to the inclined surface (b) with a smaller inclination angle of 1° than that of the liquid supply stop zone of the bottom 18a of the liquid supply tube insertion channel 18. In this way, it is possible to supply liquid at a slight rate. To supply liquid at a very high rate, the roller 13 is moved to a position corresponding to the inclined surface (c) with a greater inclination angle of 3° than that of the slight flow rate zone.

In the above embodiment the inclined surfaces (a) and (c) are provided as second and third inclined surfaces with a greater inclination angle than that of the inclined surface (b) as the first inclined surface such that they terminate at the opposite ends of the inclined surface (b). However, this is by no means limitative; for instance, it is possible to provide only a single second inclined surface terminating at either end of the first inclined surface. Further, although the creep prevention ridges 20a and 20b are provided on the side of the liquid supply tube insertion channel 18, it is possible to provide ridges on the side of the roller 13 as well.

Using the above embodiment of the device, measurement of the drop number control range was conducted by also using a comparative or contrast device, which had the same housing length but with a constant liquid supply tube insertion channel bottom inclination surface angle of 2°.

The embodiment and contrast flow control devices were each assembled in a liquid transfer set (with a liquid supply tube with an outer diameter of 3.3 mm and a wall thickness of 0.6 mm and a drop size of approximately 1/15 cc in one case and approximately 1/60 cc in another case) and connected to a liquid transfer bag. Positions of the roller corresponding to 0, 60 and 120 drops per minute were measured with a head of 1 m to obtain distances covered by the roller corresponding to 0 to 60 drops per minute and 60 to 120 drops per minute. The results are shown in Tables 4 and 5.

TABLE 4

| | (Drop size of approximately 1/15 cc, n = 10) | |
|---|---|---|
| | Distance covered by roller (mm) | |
| | 0–60 drops/min Ave. (min. to max.) | 60–120 drops/min Ave. (min. to max.) |
| Embodiment | 4.5 (2.5 8.5) | 2.5 (0.5 6.3) |
| Contrast | 2.9 (2.4 3.8) | 1.2 (0.3 1.7) |

TABLE 5

| | (Drop size of approximately 1/60 cc, n = 10) | |
|---|---|---|
| | Distance covered by roller (mm) | |
| | 0–60 drops/min Ave. (min. to max.) | 60–120 drops/min Ave. (min. to max.) |
| Embodiment | 4.3 (1.8 8.5) | 1.0 (0.3 2.1) |
| Contrast | 1.8 (1.5 2.6) | 0.4 (0.2 0.6) |

As is seen from the results, with the embodiment of the flow control device greater distance can be covered by the roller with the same housing length and same drop number change. This means that it is possible according to the invention to readily obtain adjustment to a desired position.

With the contrast flow control device having a constant liquid supply tube insertion channel bottom inclined surface angle, all flow rate ranges can not be ensured unless the inclination angle is reduced and the housing length is increased to obtain the same level of distance covered by the roller as in the case of the embodiment (i.e., obtain the same readiness of adjustment as in the case of the embodiment).

As has been shown, with the above embodiment of the flow control device, a portion of the bottom surface of the liquid supply tube insertion channel in the housing that co-operates with the roller for squeezing the liquid supply tube to control the flow rate therein comprises at least a first inclined surface providing a slight flow rate and a second inclined surface with a greater inclination angle than the first inclined surface. With this arrangement, the distance covered by the roller can be extended to facilitate the flow rate control by reducing the inclination angle of the first inclined surface, while the second inclined surface corresponding to a high flow rate range permits flow rate control without spoiling the readiness of flow control in the slight flow rate range. It is thus possible to ensure all flow rate ranges with a compact housing length.

Further, with the provision of the ridges on opposite edges of the bottom of the liquid supply tube insertion channel in the housing and also on opposite edges of the roller periphery in contact with the liquid supply tube, it is possible to prevent changes in the flow rate in long use that might otherwise result from the phenomenon of creep in the liquid supply tube, thus further improving the accuracy of the flow control.

What is claimed is:

1. A flow control device with a flexible liquid supply tube mounted therein such that said flexible liquid supply tube can be squeezed by virtue of its flexibility to vary the size of a liquid flow path in said liquid supply tube, to thereby control a rate of flow of liquid through said liquid supply tube, said flow control device comprising:

a housing having a liquid supply tube insertion channel, through which said liquid supply tube is inserted, said housing having opposite side walls which have bearing grooves therein which extend in the longitudinal direction of said liquid supply tube insertion channel, said liquid supply tube insertion channel having a bottom; and a roller having a shaft supported in said bearing grooves such that said roller is movable along said bearing grooves and along said liquid supply tube insertion channel from one end to the other end, said liquid supply tube in said liquid supply tube insertion channel being squeezed by the periphery of said roller;

said bottom of said liquid supply tube insertion channel including at least first, second and third inclined surface portions all which are inclined with respect to said bearing grooves and which are selectively cooperative with said roller to squeeze said liquid supply tube therebetween for control of the rate of flow of liquid through said liquid supply tube, said first inclined surface portion being inclined at a given angle and being adapted for fine adjustment of rate of flow of liquid through said liquid supply tub;

said second inclined surface portion being inclined in the same direction as said first inclined surface portion but by a greater angle than said first inclined surface portion and being adapted for a coarser adjustment of the rate of liquid flow through said liquid supply tube said second inclined surface portion terminating at one end portion thereof at one end portion of said first inclined surface portion;

said third inclined surface portion being inclined in the same direction as said first inclined surface portion but by a greater angle than said first inclined surface portion and being adapted for a coarser adjustment of the rate of liquid flow through said liquid supply tube, said third inclined surface portion terminating at one end portion thereof at another end portion of said first inclined surface portion such that said first inclined surface portion for said fine adjustment is located between said second and third inclined surface portions for said coarser adjustment; and the length of said first inclined surface portion being grater than the lengths of said second and third inclined surface portions.

2. The flow control device according to claim 1, further comprising urging means for urging opposite edges of said liquid supply tube inserted in said liquid supply tube insertion channel toward at least one of said roller and said bottom of said liquid supply tube insertion channel.

3. The flow control device according to claim 2, wherein said urging means comprises a pair of ridges extending along the opposite edges of said bottom of said liquid supply tube insertion channel in the direction of movement of said roller and in a range of movement of said roller.

4. The flow control device according to claim 3, wherein said ridges are substantially continuous and have rounded top portions.

5. The flow control device according to claim 2, wherein said urging means comprises a pair of ridges on opposite side edge portions of the periphery of said roller.

6. The flow control device according to claim 1, wherein the inclination angles of said first and second inclined surface portions are substantially 1° and 3°, respectively.

7. The flow control device according to claim 1, wherein the inclination angle of said third inclined surface portion is substantially 2°.

8. The flow control device according to claim 7, wherein the inclination angles of said first and second inclined surface portions are substantially 1° and 3°, respectively.

* * * * *